(12) United States Patent
Ooi et al.

(10) Patent No.: US 7,890,156 B2
(45) Date of Patent: Feb. 15, 2011

(54) MEDICAL IMAGE DISPLAY METHOD AND APPARATUS

(75) Inventors: Masao Ooi, Chiba (JP); Hiroshi Takagi, Chiba (JP); Yoshihiro Goto, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 1127 days.

(21) Appl. No.: 10/569,998

(22) PCT Filed: Sep. 9, 2004

(86) PCT No.: PCT/JP2004/013139

§ 371 (c)(1),
(2), (4) Date: Feb. 28, 2006

(87) PCT Pub. No.: WO2005/025422

PCT Pub. Date: Mar. 24, 2005

(65) Prior Publication Data

US 2007/0053555 A1    Mar. 8, 2007

(30) Foreign Application Priority Data

Sep. 10, 2003   (JP) .............................. 2003-317613

(51) Int. Cl.
*A61B 5/05*   (2006.01)

(52) U.S. Cl. ............ 600/425; 600/431; 600/476; 382/128; 382/130; 382/131; 382/132; 378/4; 378/21; 378/62

(58) Field of Classification Search .......... 600/425, 600/431, 476; 378/4, 21, 62; 382/128, 130
See application file for complete search history.

(56) References Cited

U.S. PATENT DOCUMENTS

| | | | | |
|---|---|---|---|---|
| 5,507,287 A | * | 4/1996 | Palcic et al. | 600/317 |
| 6,174,291 B1 | * | 1/2001 | McMahon et al. | 600/564 |
| 6,711,433 B1 | * | 3/2004 | Geiger et al. | 600/431 |
| 6,721,590 B2 | * | 4/2004 | Ohishi et al. | 600/431 |
| 6,842,638 B1 | * | 1/2005 | Suri et al. | 600/425 |
| 7,474,776 B2 | * | 1/2009 | Kaufman et al. | 382/128 |
| 7,505,549 B2 | * | 3/2009 | Ohishi et al. | 378/4 |
| 2007/0014452 A1 | * | 1/2007 | Suresh et al. | 382/128 |

FOREIGN PATENT DOCUMENTS

| | | |
|---|---|---|
| JP | 2000-175897 | 6/2000 |
| JP | 2001-149361 | 6/2001 |
| JP | 2001-283191 | 10/2001 |
| JP | 2002-95654 | 4/2002 |
| JP | 2003-10172 | 1/2003 |
| JP | 2003-33349 | 2/2003 |

* cited by examiner

*Primary Examiner*—Brian Casler
*Assistant Examiner*—Baisakhi Roy
(74) *Attorney, Agent, or Firm*—Cooper & Dunham LLP (57) ABSTRACT

A medical image display method of this invention includes an organ display step for displaying an image of a predetermined organ including a desired blood vessel in a medical image on a display unit; a blood vessel selection step for selecting the desired blood vessel from the image of the predetermined organ displayed by the organ display step and designating a specific position of the desired blood vessel; and an image display step for displaying a pseudo image in a pseudo imaging mode as if a contrast agent were made to flow through the blood vessel selected in the blood vessel selection step. The pseudo image of the flow of the contrast agent in the blood vessel assists doctor in conducting diagnoses and therapies.

20 Claims, 12 Drawing Sheets

MEDICAL IMAGE DISPLAY METHOD AND APPARATUS

TECHNICAL FIELD

This invention relates to a medical image display method and a medical image display apparatus assisting doctors in conducting diagnoses and therapies by displaying in a pseudo manner a flow of a contrast agent introduced in a pseudo manner by a doctor in a clinical practice into a blood vessel related to an organ in a living body, such as a liver.

BACKGROUND ART

In recent years, a medical image which is obtained by a medical diagnostic imaging device such as an X-ray imaging apparatus, an x-ray CT apparatus, and an MRI apparatus has actively been used not only for conducting diagnosis but also for conducting a therapy.

Examples of the use for therapy include a method of extracting a specific part of an organ in advance of a surgery, and the method is disclosed in Patent Literature 1. A description of the extraction of specific part of organ based on a state of a blood vessel running in the organ is given in Patent Literature 1.

However, Patent Literature 1 does not consider a use, for a doctor's diagnosis and therapy, of a pseudo display of a flow of a contrast agent introduced in a pseudo manner by the doctor in a clinical practice into a blood vessel relating to an organ in a living body, such as a liver.

Patent Literature 1: JP-A-2001-283191

DISCLOSURE OF THE INVENTION

A medical image display method of this invention comprises: an organ display step for displaying an image of a predetermined organ including a desired blood vessel in a medical image; a blood vessel selection step for selecting the desired blood vessel from the image of the predetermined organ displayed by the organ display step and designating a specific position of the desired blood vessel; and an image display step for displaying a pseudo image in a pseudo imaging mode as if a contrast agent were made to flow through the blood vessel selected in the blood vessel selection step.

Thus, the medical image display method assists doctors in conducting diagnoses and therapies by displaying the contrast agent flow in the blood vessel in the pseudo manner.

Also, in view of the fact that the flow of the contrast agent in a blood vessel can be a burden for patients since the contrast agent cannot be injected into a body of some patients depending on her/his constitution, the pseudo imaging mode with which the contrast agent is made to flow through the blood vessel in the pseudo manner is beneficial for the patients.

According to the preferred embodiment of this invention, the medical image display method further comprises: a tissue border calculation step for calculating a tissue border of a related region relating to the desired blood vessel selected by the blood vessel selection step, wherein the image display step in the pseudo imaging mode enables to display a pseudo image as if the contrast agent were made to flow from the specified position to the selected blood vessel and the related region of the blood vessel based on the tissue border calculated by the tissue border calculation step. Thus, it is possible to display in the pseudo manner the flow of the contrast agent in the related region to be influenced by the contrast agent injected into the blood vessel.

According to the preferred embodiment of this invention, the image display step in the pseudo imaging mode comprises sequentially displaying the pseudo flow of the contrast agent from the specified position to the related region calculated by the tissue border calculation step.

Thus, it is possible to display states of gradual circulation of the contrast agent, which is injected into the blood vessel, in the blood vessel and the tissue in the pseudo manner with high accuracy.

According to the preferred embodiment of this invention, the blood vessel selection step comprises setting a region of interest in extracting the image of the predetermined organ, and the tissue border calculation step comprises calculating the tissue border based on the set region of interest. Thus, since the calculation object is limited to the region of interest, it is possible to reduce a calculation time as compared to the case where calculation object is the overall organ.

According to the preferred embodiment of this invention, the blood vessel selection step comprises arbitrarily setting the specified position in the desired blood vessel as a virtual contrast agent injection start position.

Thus, it is possible to set the contrast agent injection start position arbitrarily and to display in a pseudo manner the flow of the contrast agent from the arbitrarily set start point in the blood vessel and the tissue.

According to the preferred embodiment of this invention, the medical image display method further comprises a step for setting a termination position corresponding to the injection start position, wherein the image display step in the pseudo imaging mode comprises sequentially displaying a pseudo image of a flow of the contrast agent from the injection start position to the termination position.

Thus, since it is possible to set a range, of the virtual contrast agent, which is an observation object, by setting the start position and the termination position arbitrarily, it is possible to further increase a degree of freedom for setting the contrast agent observation range.

According to the preferred embodiment of this invention, the image display step in the pseudo imaging mode comprises sequentially displaying a pseudo image of a flow of the contrast agent to a substantially whole part of the related region of the selected blood vessel.

Thus, since it is possible to observe the flow of the contrast agent to the substantially whole part of the related region in the pseudo manner only by selecting the desired blood vessel, it is possible to display the flow of the contrast agent in the selected blood vessel by such single operation.

According to the preferred embodiment of this invention, the image display step in the pseudo imaging mode comprises sequentially highlighting a locus of the flow of the contrast agent in displaying the pseudo image.

Thus, it is possible for an observer to identify at a glance a position to which the contrast agent which flows in the pseudo manner has reached in the blood vessel of the observation object sequentially displayed.

According to the preferred embodiment of this invention, the highlighting comprises marking out the locus with a predetermined color or luminance. Since the marking out is performed for the purpose of displaying the pseudo circulation of the contrast agent in the blood vessel in relation to a circumference, the marking out includes various display modes such as a color change and a blinking display of the locus.

Thus, it is possible for the observer to clearly identify at a glance a position to which the contrast agent which flows in the pseudo manner has reached in the blood vessel of the observation object sequentially displayed.

According to the preferred embodiment of this invention, the image display step in the pseudo imaging mode comprises sequentially displaying a pseudo image of a flow of the contrast agent from the predetermined position of the blood vessel selected by the blood vessel selection step to a periphery of the blood vessel.

Thus, it is possible to observe states of the pseudo circulation of the contrast agent in the blood vessel sequentially from the position of the blood vessel which is the observation object to the periphery of the blood vessel.

A medical image display apparatus of this invention comprises: an organ display unit for displaying an image of a predetermined organ including a desired blood vessel in a medical image on a display unit; a blood vessel selection unit for selecting the desired blood vessel from the image of the predetermined organ displayed by the organ display unit and designating a specific position of the desired blood vessel; and an image display unit for displaying a pseudo image in a pseudo imaging mode as if a contrast agent were made to flow through the blood vessel selected in the blood vessel selection unit.

Thus, the medical image display apparatus assists doctors in conducting diagnoses and therapies by displaying the flow of the contrast agent in the blood vessel in the pseudo manner.

BEST MODE FOR CARRYING OUT THE INVENTION

Figure 1:
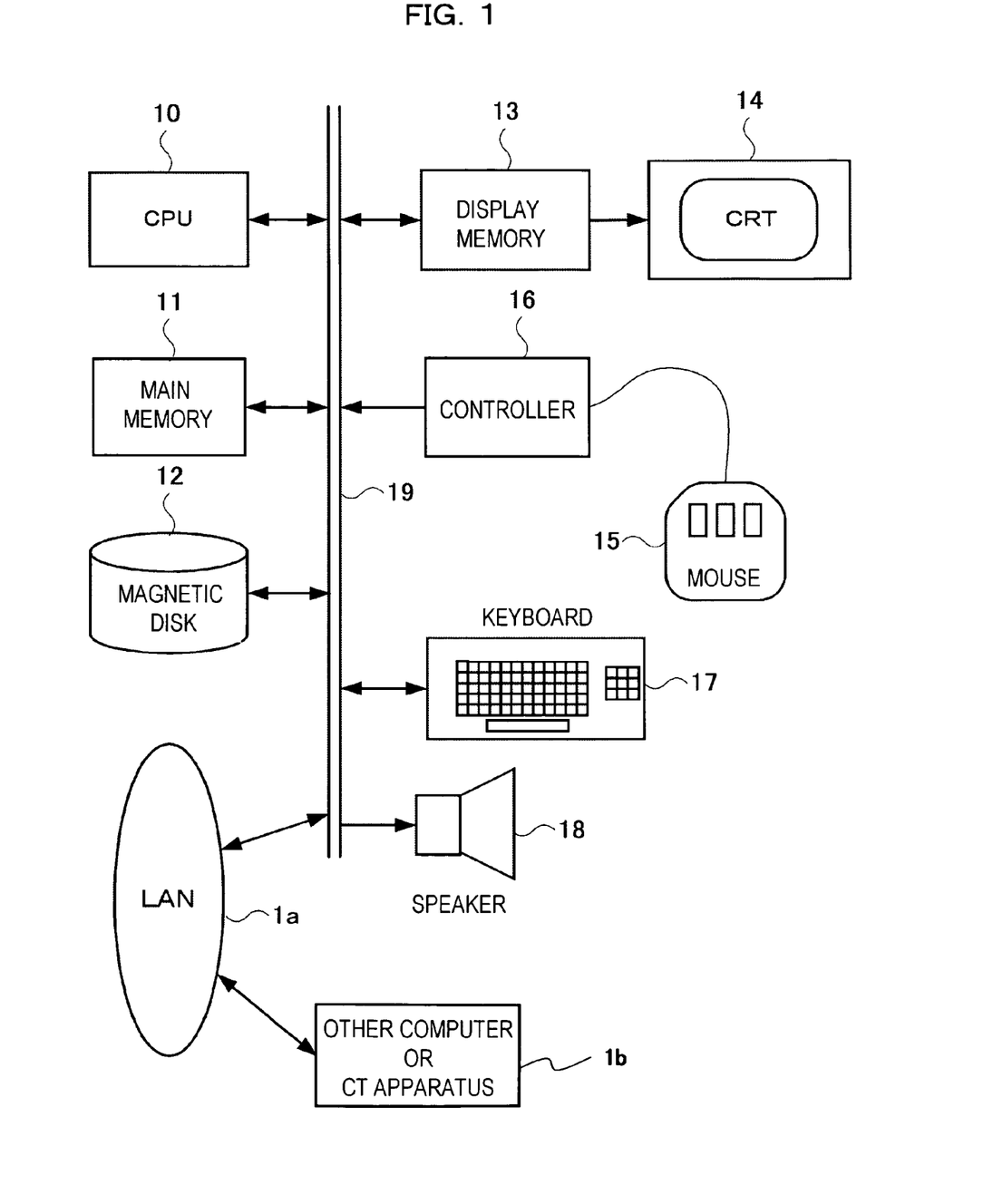
[FIG. 1] A block diagram showing a hardware constitution of an overall medical image display apparatus to which this invention is applied.

Preferred embodiments of a medical image display apparatus and a medical image display method according to this invention will be described with reference to the accompanying drawings. FIG. 1 is a block diagram showing a hardware constitution of an overall medical image display apparatus to which this invention is applied. The medical image display apparatus uses an X-ray CT image of a liver obtained by contrast imaging as a processing object and blood vessel running information to display a procedure of specifying a region of the liver and to display a removal region of the liver by using the procedure. The medical image display apparatus is provided with a central processing unit (CPU) 10 for controlling operations of component parts, a main memory 11 in which a control program for the overall apparatus is stored, a magnetic disk 12 in which a plurality of series of tomogram data and programs are stored, a display memory 13 for temporarily storing image data to be displayed, a CRT display 14 used as a display unit for displaying an image based on the image data from the display memory 13, a mouse 15 for operating soft switches displayed on a screen, and a controller 16 for the mouse 15, a keyboard 17 having keys and switches for setting various parameters, a speaker 18, and a common bus 19 for connecting the above-described component parts.

Though only the magnetic disk 12 is connected as the storage other than the main memory 11 in this embodiment, a floppy disk drive, a hard disk drive, a CD-ROM drive, a magnetooptical disk drive, a ZIP drive, a PD drive, a DVD drive, and/or the like may be connected. Also, the image data may be communicated with other computers or a CT apparatus 1b via a communication interface by interconnecting on a communication network 1a such as a LAN (Local Area Network), the internet, a telephone line, and the like. The image data communication may be performed by connecting a medical image display apparatus capable of collecting tomograms of an examinee, such as an X-ray CT apparatus and an MRI apparatus, to the communication network 1a such as the LAN.

Figure 2:
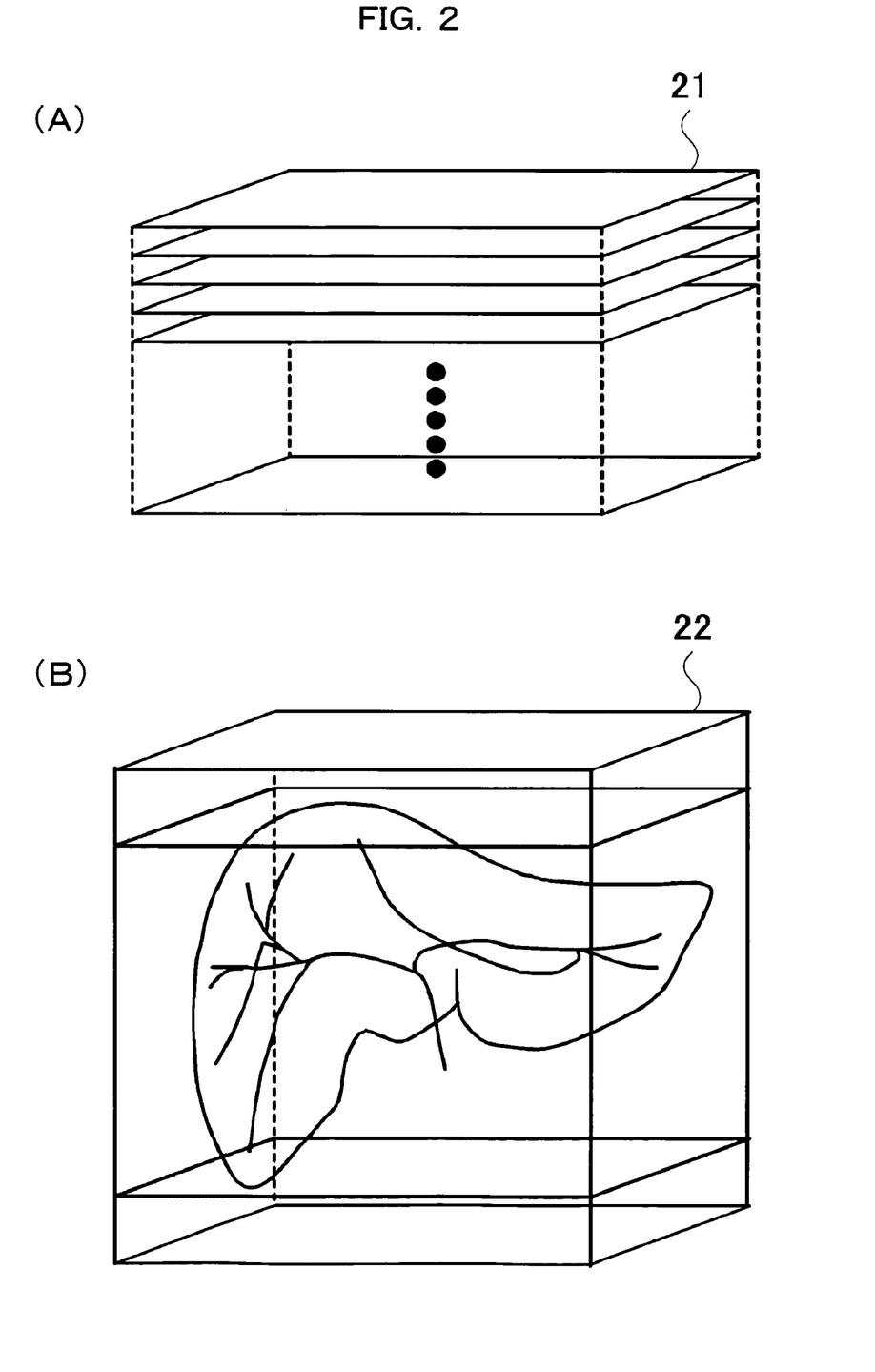
[FIG. 2] A diagram showing a relationship between tomograms and data.

Hereinafter, a first operation example of the medical image display apparatus of FIG. 1 will be described with reference to the drawings. FIG. 2 is a diagram showing a relationship between tomogram and data. As shown in FIG. 2(A), a plurality of tomograms 21 obtained by an diagnostic imaging apparatus capable of three-dimensional measurement, such as an X-ray CT apparatus and an MRI apparatus, are stacked to form a stacked three-dimensional image 22 shown in FIG. 2(B) to obtain a three-dimensional image of a predetermined organ (processing object). The stacked three-dimensional image 22 includes tissues, arteries, veins, tumors of a liver and is displayed on the CRT display 14 of FIG. 1, for example, as a quasi three-dimensional image obtained by performing shadow-casting on a two-dimensional projection plane (not shown).

Figure 3:
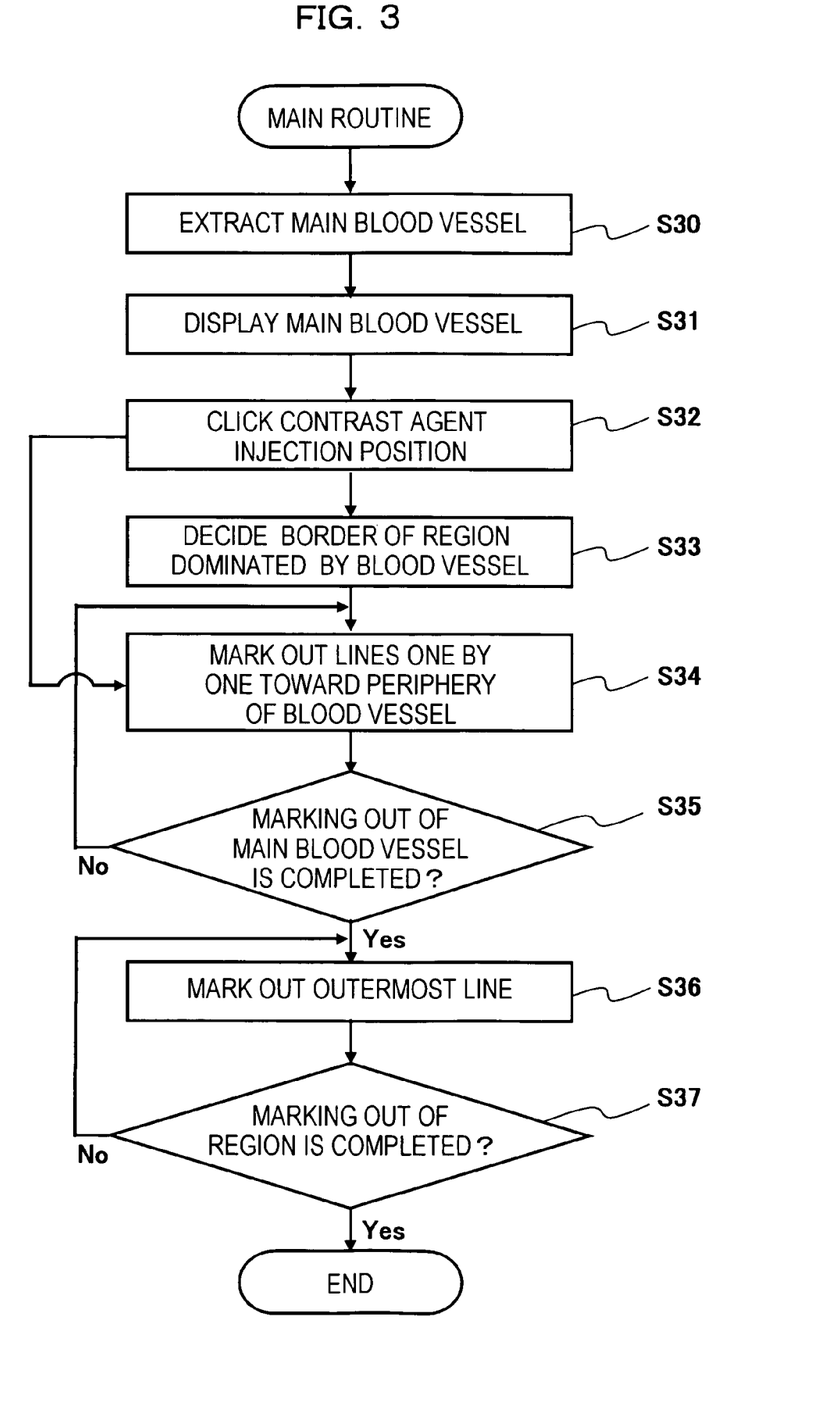
[FIG. 3] A diagram showing one example of a main flowchart of a pseudo imaging display mode performed by the medical image display apparatus.

FIG. 3 is a diagram showing one example of a main flowchart of a pseudo imaging display mode performed by the medical image display apparatus. The CPU 10 of FIG. 1 operates in accordance with the main flowchart. With reference to the main flowchart, changes with time in the case where a contrast agent is injected into one of the blood vessels of the liver will be described by the use of one example of images displayed on the CRT display 14. Hereinafter, details of the main flowchart will be described in the order of steps.

[Step S30]

A main blood vessel is extracted from the three-dimensional image. The extraction of main blood vessel is performed by a known region growing method or the like. With the region growing method, when adjacent pixels satisfy a condition such as a CT value, the pixels are considered to be an identical region in the extraction.

[Step S31]

Figure 4:
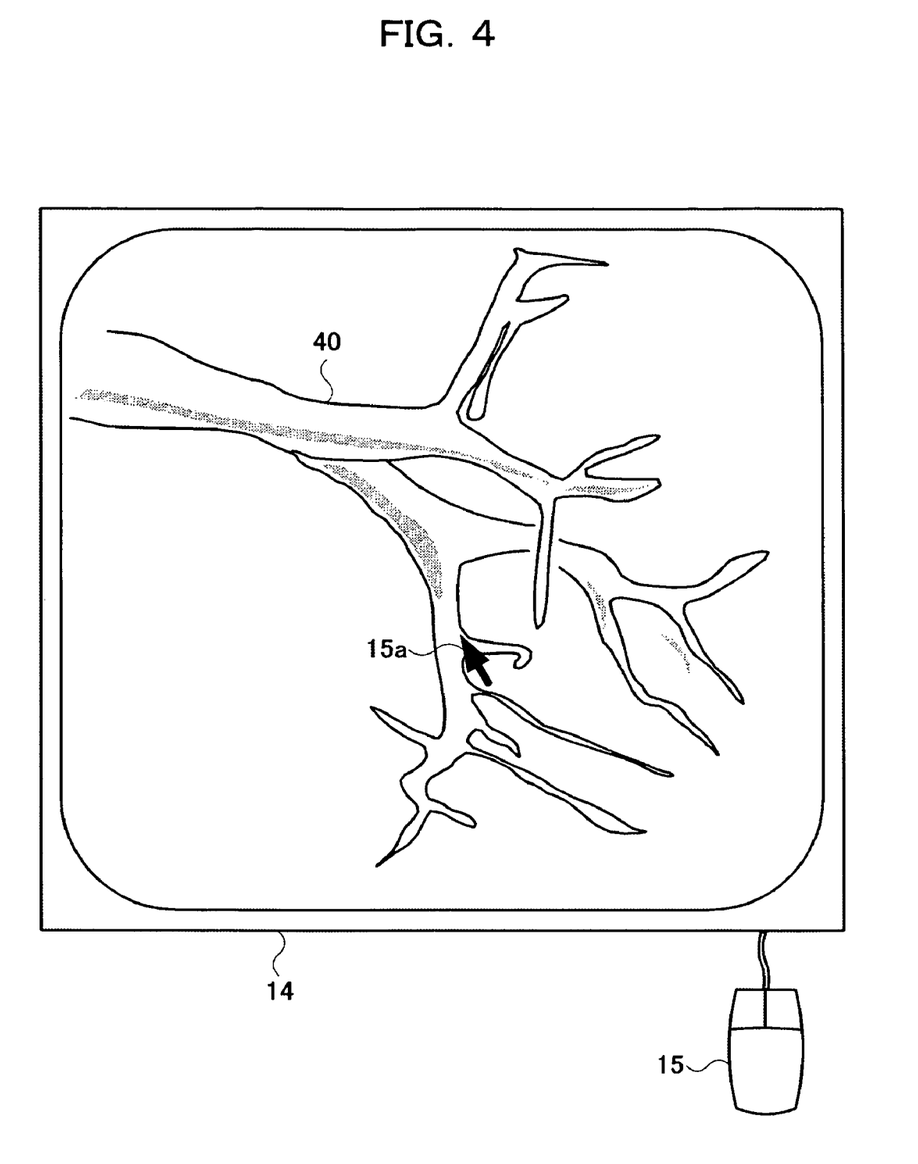
[FIG. 4] A diagram showing one example of a main blood vessel displayed on a CRT display 14.

The main blood vessel extracted by the region growing method in Step S30 is displayed on the CRT display 14. FIG. 4 is a diagram showing one example of the extracted main blood vessel.

[Step S32]

Figure 5:
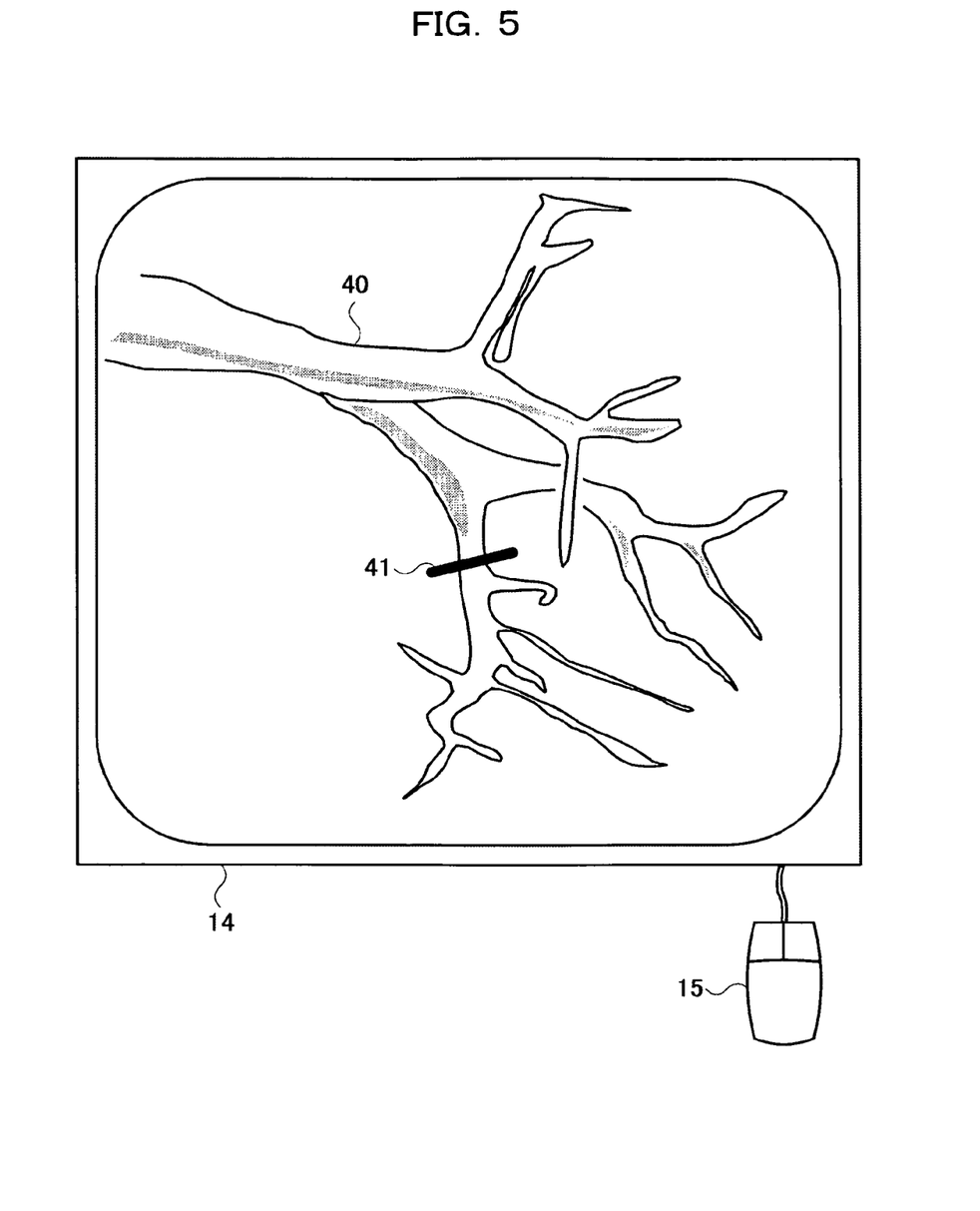
[FIG. 5] A diagram showing a state of the main blood vessel after a click.

A cursor 15a of the mouse 15 is moved to the main blood vessel displayed on the CRT display 14 to select and click on a contrast agent injected portion. With this operation, an injection position line 41 indicating from which part the contrast agent has been injected to the main blood vessel 40 is displayed as shown in FIG. 5.

[Step S33]

Step S33 is skipped in the first operation example.

[Step S34]

A locus from the contrast agent injection position, i.e., the injection position line 41 to a periphery of the blood vessel are highlighted. For instance, a line extending from the injection position line 41 to the periphery of the blood vessel is marked out in the drawing. That is, with an approximation that a flow rate inside the blood vessel is constant, lines are added in the blood vessel with respect to the injection position line 41 one by one (plural line may be added at once), and the addition of lines is displayed on the CRT display 14. Under the assumption that the flow rate V in the blood vessel is constant, a relationship between a product $S0 \times V0$ of a sectional area $S0$ of the blood vessel immediately after the injection position line 41 and a flow rate $V0$ immediately after the injection position line 41 and sectional areas $S1$ and $S01$ of diverging blood vessels immediately after the sectional area $S0$ and flow rates $V1$ and $V01$ is represented by the following equation (1).

$$S0 \cdot V0 = S1 \cdot V1 + S01 \cdot V01 \quad (1)$$

In the same manner, relationships between sectional areas $S2$ to $Sn$ and $S02$ to $S0n$ and flow rates $V2$ to $Vn$ and $V02$ to $V0n$ of diverging blood vessels immediately after the sectional area $S01$ are represented by the following expression (2).

$$S01 \cdot V01 = S2 \cdot V2 + S02 \cdot V02$$

$$S02 \cdot V02 = S3 \cdot V3 + S03 \cdot V03$$

$$S03 \cdot V03 = S4 \cdot V4 + S03 \cdot V03$$

$$\ldots$$

$$S0n \cdot V0n = Sn \cdot Vn + Sn-1 \cdot Vn-1 \quad (2)$$

Figure 8:
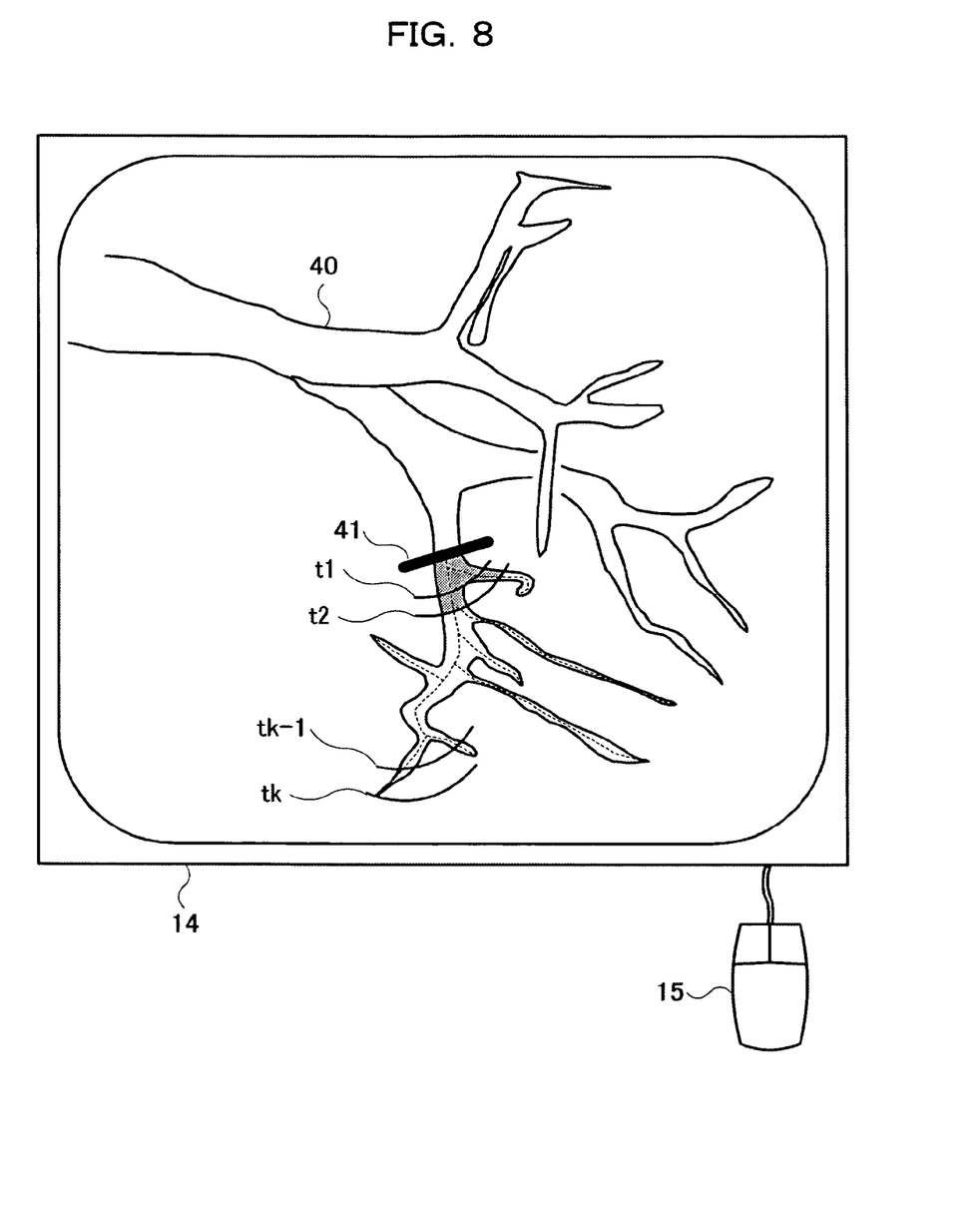
[FIG. 8] A diagram showing a relationship between a flowing blood and a time.

In this embodiment, the flow rate in the capillary blood vessel is approximated to be constant for brevity. Therefore, the marking out of the lines starts from the time at which the mouse 15 was clicked, and then the lines are marked out one by one in the order of times t1, t2, ..., tk−1, and tk as shown in FIG. 4. In FIG. 8, a region marked out from the injection position line 41 of the main blood vessel 40 to the periphery during a period from the click of the mouse 15 to the time t2 is indicated by a half-tone dot meshing.

[Step S35]

Figure 9:
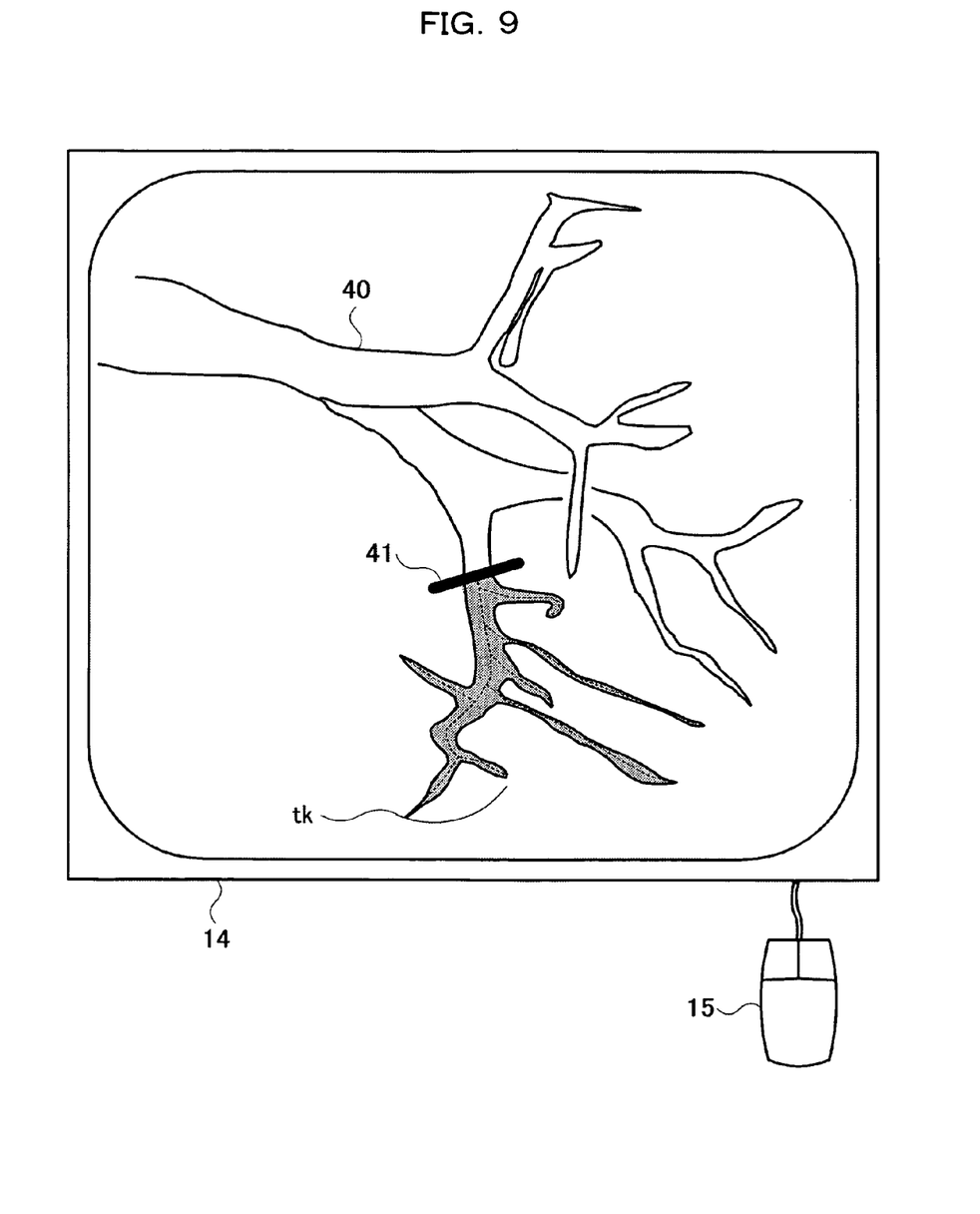
[FIG. 9] A diagram showing a state in which the flowing blood has reached to a periphery of a blood vessel at a time tk.

It is judged whether or not the marking out of the main blood vessel has been completed, and the process returns to Step S34 when the marking out has not been completed (no) to perform the line marking out processing one line after the other line. In the case where it is judged that the marking out has been completed (yes), the process proceeds to the next step S36. The making out processing of the main blood vessel is performed as described above, and, when the marking out processing is performed on the periphery of the main blood vessel 40 at the time tk, a whole portion extending from the injection position line 41 of the main blood vessel 40 is marked out to be displayed as the half-tone dot meshing portion as shown in FIG. 9. At this time point, the judgment of Step S35 is "yes" to perform processing of the next step S36.

[Step S36]

In this step, processing for indicating intermediary states of the flow of the blood containing the contrast agent to the tissue via the capillary blood vessel is performed, wherein lines are added outside the blood vessel one by one (plural lines may be added at once) adjacent to the outermost line of the marked out main blood vessel 40 to be marked out.

[Step S37]

Figure 10:
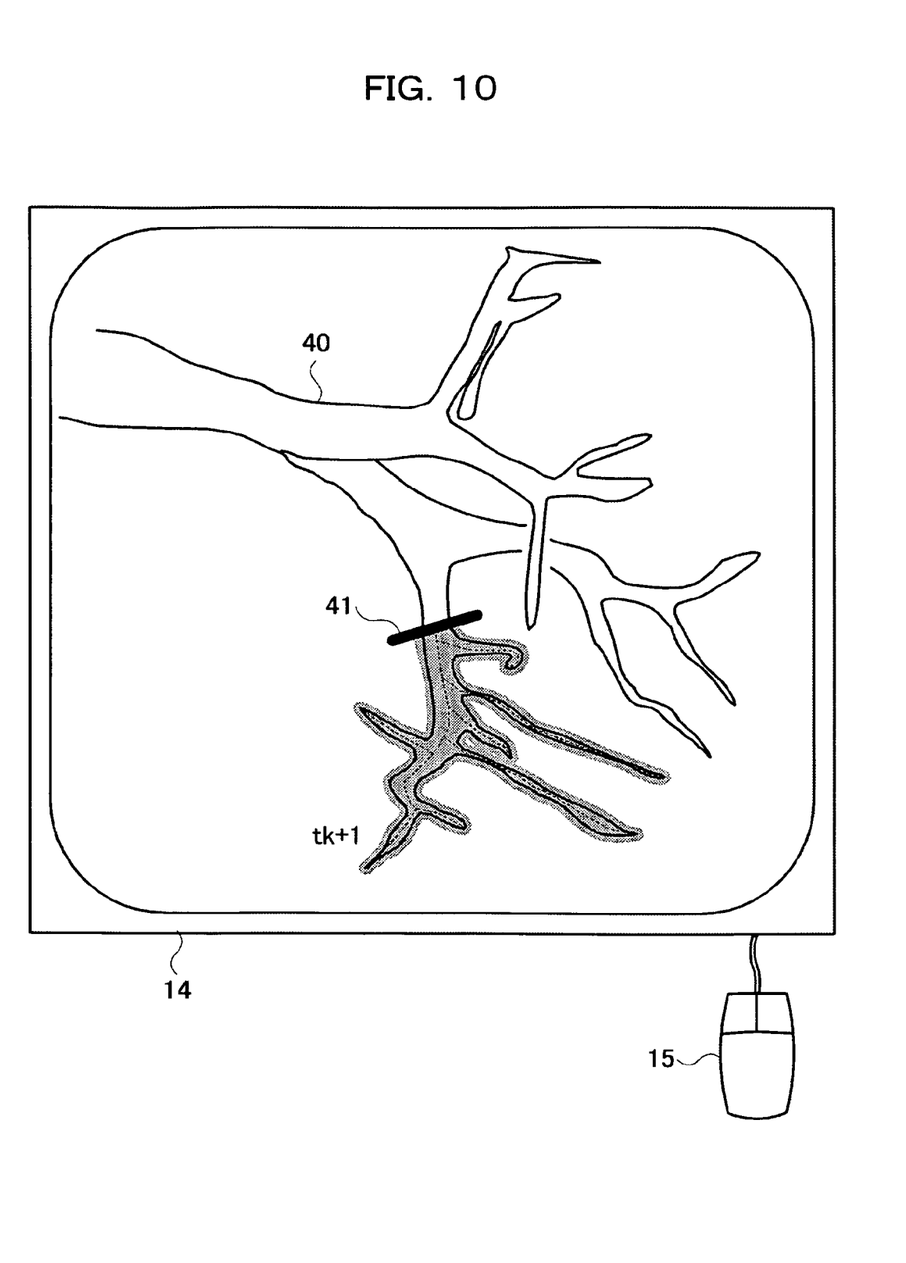
[FIG. 10] A diagram showing a state in which the flowing blood has flown out via a capillary blood vessel at a time tk+1.
Figure 11:
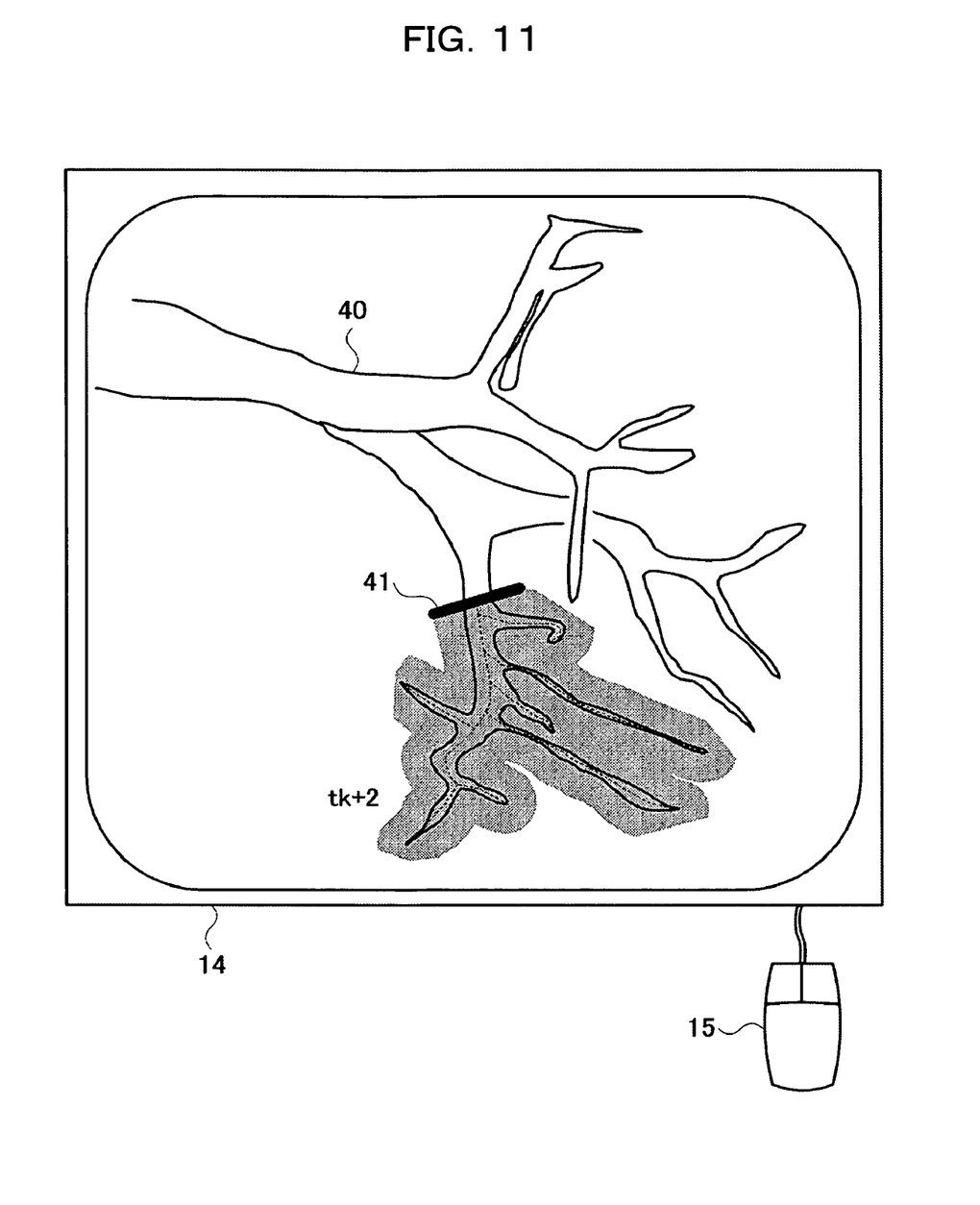
[FIG. 11] A diagram showing a state in which the flowing blood has flown out via the capillary blood vessel at a time tk+2.
Figure 12:
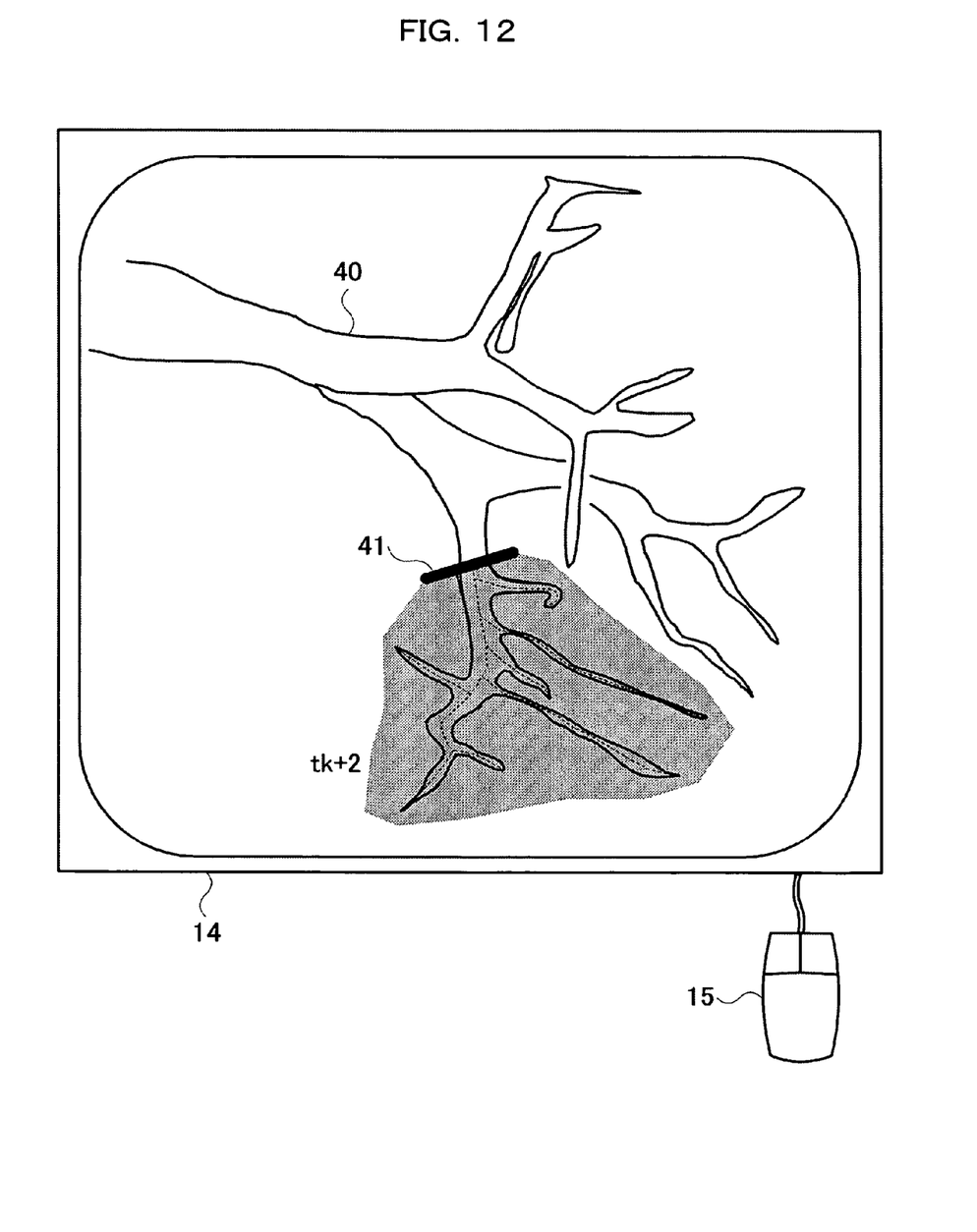
[FIG. 12] A diagram showing a state in which a contrast agent has spread all over the region dominated by the blood vessel.

It is judged whether or not the tissue marking out has been completed, and the process returns to Step S36 when the making out has not been completed (no) so that the marking out processing on each of the lines outside the blood vessel is performed. When it is judged that the processing has been completed (yes), the process is brought to an end. The marking out processing on the dividing border is performed as described above. Shown in FIG. 10 is a state in which each of the lines outside the main blood vessel 40 has been marked out at the time tk+1 after the whole part of the main blood vessel 40 including its periphery was marked out. When the time has elapsed to the time tk+2, the part of the main blood vessel 40 extending from the injection position line 41 is marked out, and the blood containing the contrast agent exudes out of the blood vessel as shown in FIG. 11. A limit of the exudation is a region in which the main blood vessel is involved, and the exudation does not occur outside the region. The gradual exudation of blood to the tissue is displayed on the CRT display 14, and, ultimately, the whole part of the tissue detected in Step S34 is indicated by the half-tone dot meshing as shown in FIG. 12 to terminate the processing.

Thus, since the apparatus is capable of displaying the main blood vessel and the flow of contrast agent in the tissue relating to the main blood vessel in the pseudo manner, the apparatus is useful for doctor's diagnosis and therapy.

Also, in view of the fact that flow of the contrast agent in a blood vessel can be a burden for patients since the contrast agent cannot be injected into a body of some patients depending on her/his constitution, the pseudo imaging mode with which the contrast agent is made to flow through the blood vessel in the pseudo manner is beneficial for the patients.

Hereinafter, a second operation example of the medical image display apparatus of FIG. 1 will be described with reference to the drawings. FIG. 2 is a diagram showing a relationship between tomograms and data. As shown in FIG. 2(A), a plurality of tomograms 21 obtained by an diagnostic imaging apparatus capable of three-dimensional measurement, such as an X-ray CT apparatus and an MRI apparatus, are stacked to form a stacked three-dimensional image 22 shown in FIG. 2(B) to obtain a three-dimensional image of a predetermined organ (processing object). The stacked three-dimensional image 22 includes tissues, arteries, veins, tumors of a liver and is displayed on the CRT display 14 of FIG. 1, for example, as a quasi three-dimensional image obtained by performing shadow-casting on a two-dimensional projection plane (not shown). Though the three-dimensional image is used as an example of the displayed image of predetermined organ, an MPR (Multi Planner Reconstruction) image formed of a plurality of two-dimensional images may be used in place of the three-dimensional image.

FIG. 3 is a diagram showing one example of a main flowchart of a pseudo imaging display mode performed by the medical image display apparatus. The CPU 10 of FIG. 1 operates in accordance with the main flowchart. With reference to the main flowchart, changes with time in the case where a contrast agent is injected to one of the blood vessels of the liver will be described by the use of one example of images displayed on the CRT display 14. Hereinafter, details of the main flowchart will be described in the order of steps.

[Step S30]

A main blood vessel is extracted from the three-dimensional image. The extraction of main blood vessel is performed by a known region growing method or the like. With the region growing method, when adjacent pixels satisfy a condition such as a CT value, the pixels are considered to be an identical region in the extraction. In extracting the main blood vessel, a region of interest may be set to reduce an amount of calculations for the blood vessel extraction and related region extraction by the use of the region of interest, thereby achieving high speed extraction and calculation.

[Step S31]

The main blood vessel extracted by the region growing method in Step S30 is displayed on the CRT display 14. FIG. 4 is a diagram showing one example of the extracted main blood vessel.

[Step S32]

A cursor 15*a* of the mouse 15 is moved to the main blood vessel displayed on the CRT display 14 to select and click on a contrast agent injected portion. With this operation, an injection position line 41 indicating from which part the contrast agent has been injected to the main blood vessel 40 is displayed. Since it is possible to set the injection start position arbitrarily, it is possible to display in a pseudo manner a flow of a contrast agent in the blood vessel and the tissue from the arbitrarily set start point.

Also, a start point and a termination point of a range of a virtual contrast agent, which is an observation object, may be set arbitrarily so as to increase a degree of freedom for setting an observation range of the blood flow and the pseudo contrast agent flow.

Further, a pseudo observation of a flow of the contrast agent in substantially whole part of the related region may be enabled only by a selection of the desired blood vessel so as to simulate the flow of contrast agent in the blood vessel selected by such single operation.

[Step S33]

Figure 6:
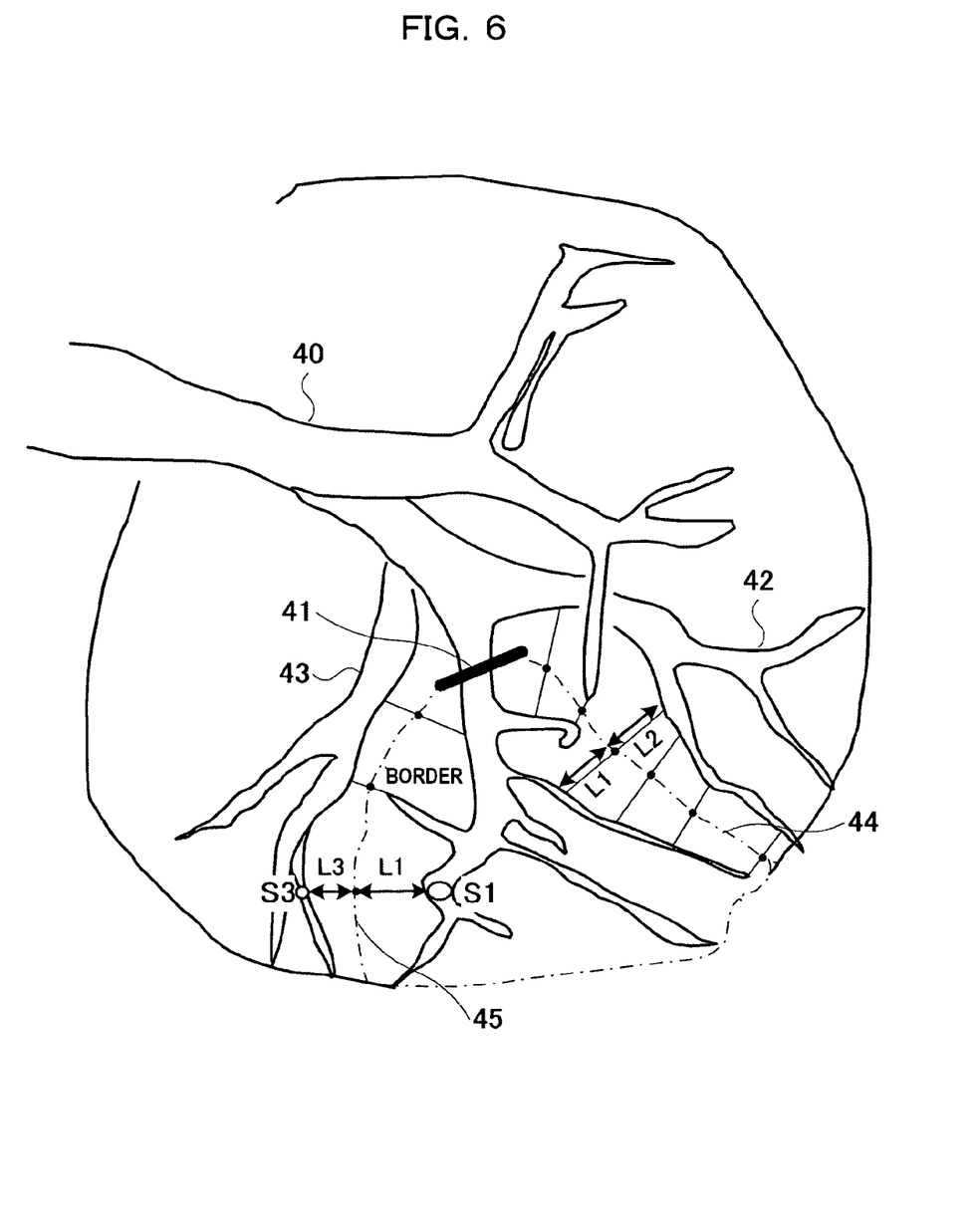
[FIG. 6] A diagram specifically showing a method of deciding a border of a region dominated by a blood vessel.
Figure 7:
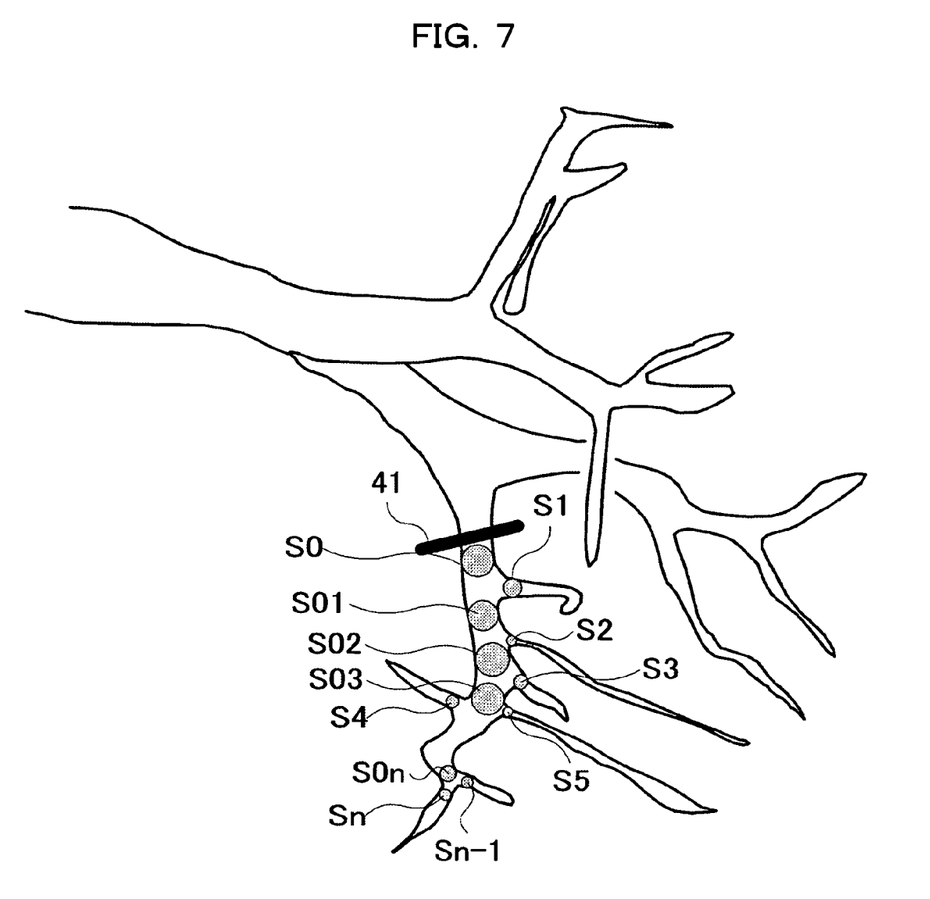
[FIG. 7] A diagram showing a general relationship between a blood vessel sectional area and a blood flow rate.

A border of a region dominated by the main blood vessel and extending from the injection position line to the periphery is decided. FIG. 6 is a diagram specifically showing a method of deciding the border of the region dominated by the blood vessel. As shown in FIG. 6, in the extracted main blood vessel 40, shortest distances between the blood vessel including the injection position line 41 indicating the position clicked with the mouse 15 and the periphery and diverted blood vessels 42 and 43 are obtained, and then each of line segments of the shortest distances is divided by a predetermined method. After that, the divided lines are connected to decide the border of the region relating to the blood vessel. The decision of region border is performed by either one of the following methods. In the first method, a shortest distance between the main blood vessel 40 including the injection position line 41 and the periphery and the diverted blood vessel 42 is obtained, and then a midpoint of a line segment L of the shortest distance is detected to set the midpoint as a division point. A case where the border decision between the main blood vessel 40 including the injection position line 41 and the periphery and the diverted blood vessel 42 is performed with the first method is shown in FIG. 6, in which a point represented by an equation of $L1=L2$ in the line segment of the shortest distance between the main blood vessel 40 including the injection position line 41 and the periphery and the diverted blood vessel 42 is the division point, and a border 44 is decided by connecting thus-obtained division points. In the second method, a shortest distance between the main blood vessel 40 including the injection position line 41 and the periphery and the diverted blood vessel 43 is obtained, and then a division point of a line segment L of the shortest distance is decided by prorating sizes (sectional areas) S1 and S3 of the blood vessels. In FIG. 6, in the line segment of the shortest distance between the main blood vessel 40 including the injection position line 41 and the periphery and the diverted blood vessel 43, a line segment ratio $L1:L3$ equivalent to a sectional area ratio $S1:S3$ is obtained, and then the ratio is used as the division point. A border 45 is decided by connecting thus-obtained division points.

A limit of the region may be set arbitrarily by arbitrarily setting a blood flow start point and a blood flow termination point of a blood flow region which is an observation object.

Also, when the limit of the region is set as a substantially whole part of a related region including the main blood vessel, the blood flow to substantially whole part of the related region can be observed only by selecting a desired blood vessel. Thus, it is possible to simulate the blood flow of the blood vessel selected by such single operation.

[Step 34]

A locus from the contrast agent injection position, i.e., the injection position line 41 to a periphery of the blood vessel are highlighted. For instance, a line extending from the injection position line 41 to the periphery of the blood vessel is marked out in the drawing. That is, with an approximation that a flow rate inside the blood vessel is constant, lines are added in the blood vessel with respect to the injection position line 41 one by one (plural line may be added at once), and the addition of lines is displayed on the CRT display 14. Under the assumption that the flow rate V in the blood vessel is constant, a relationship between a product $S0 \times V0$ of a sectional area $S0$ of the blood vessel immediately after the injection position line 41 and a flow rate $V0$ immediately after the injection position line 41 and sectional areas $S1$ and $S01$ of diverging blood vessel immediately after the sectional area $S0$ and flow rates $V1$ and $V01$ is represented by the following equation (3).

$$S0 \cdot V0 = S1 \cdot V1 + S01 \cdot V01 \qquad (3)$$

In the same manner, relationships between sectional areas $S2$ to $Sn$ and $S02$ to $S0n$ and flow rates $V2$ to $Vn$ and $V02$ to $V0n$ of diverging blood vessels immediately after the sectional area $S01$ are represented by the following expression (4).

$$S01 \cdot V01 = S2 \cdot V2 + S02 \cdot V02$$

$$S02 \cdot V02 = S3 \cdot V3 + S03 \cdot V03$$

$$S03 \cdot V03 = S4 \cdot V4 + S03 \cdot V03$$

$$\ldots$$

$$S0n \cdot V0n = Sn \cdot Vn + Sn{-}1 \cdot Vn{-}1 \qquad (4)$$

In this embodiment, the flow rate in the capillary blood vessel is approximated to be constant for brevity. Therefore, the marking out of the lines starts from the time at which the mouse 15 was clicked, and then the lines are marked out one by one in the order of times $t1, t2, \ldots, tk-1$, and $tk$. In FIG. 8, a region marked out from the injection position line 41 of the main blood vessel 40 to the periphery during a period from the click of the mouse 15 to the time $t2$ is indicated by a half-tone dot meshing.

[Step 35]

It is judged whether or not the marking out of the main blood vessel has been completed, and the process returns to Step S34 when the marking out has not been completed (no) to perform the line marking out processing one line after the other. When it is judged that the marking out has been completed (yes), the process proceeds to the next step S36. The making out processing of the main blood vessel is performed as described above, and, when the marking out processing is performed on the periphery of the main blood vessel 40 at the time tk, a whole portion extending from the injection position line 41 of the main blood vessel 40 is marked out to be displayed as the half-tone dot meshing portion as shown in FIG. 9. At this time point, the judgment of Step S35 is "yes" to perform processing of the next step S36.

[Step S36]

In this step, processing for indicating intermediary states of the flow of the blood containing the contrast agent to the division border detected in step S33 via the capillary blood vessel is performed, wherein lines are added outside the blood vessel one by one (plural lines may be added at once) adjacent to the outermost line of the marked out main blood vessel 40 to be marked out.

[Step S37]

It is judged whether or not the division border marking out has been completed, and the process returns to Step S36 when the making out has not been completed (no) so that the marking out processing on each of the lines outside the blood vessel is performed. When it is judged that the processing has been completed (yes), the process is brought to an end. The marking out processing on the division border is performed as described above. Shown in FIG. 10 is a state in which each of the lines outside the main blood vessel 40 has been marked out at the time tk+1 after the whole part of the main blood vessel 40 including its periphery was marked out. When the time has elapsed to the time tk+2, the part of the main blood vessel 40 extending from the injection position line 41 is marked out, and the blood containing the contrast agent exudes out of the blood vessel as shown in FIG. 11. A limit of the exudation is the border decided in Step S33, and the exudation does not occur outside the border. The gradual exudation of blood to the division borer is displayed on the CRT display 14, and, ultimately, a whole part of the division border detected in Step S33 is indicated by the half-tone dot meshing as shown in FIG. 12 to terminate the processing.

Thus, since the apparatus is capable of displaying the intermediary steps of the circulation of the contrast agent in the blood vessel after being injected into a part of the blood vessel, the apparatus enables to remarkably improve accuracy of doctor's simulation as preoperative planning for organ resection.

Though one position is set as the position of injection of the contrast agent in the foregoing embodiments, a plurality of points may be designated to perform simultaneous simulation. In this case, colors of marking out may be varied from one another, for example, in order to recognize the simulation with higher accuracy. Though the contrast agent is injected in the foregoing embodiments, changes to an ischemic state or a congestive state from the ligature position may be simulated in the case of a blood vessel ligature.

When displaying the thus-obtained resection area, concentrations and color phases of the extracted related region (specified region), i.e. the resection area, and other non-extracted regions are varied from each other so that an image observer distinguishes the specified area from the non-extracted easily when they are displayed on the CRT display 14.

Also, in the line marking out processing, a thickness of the line may be changed as it approaches to the periphery of the blood vessel from the specified position. That is, the line thickness may be increased for a thick blood vessel or may be reduced for a thinner blood vessel. By thus changing the line thickness corresponding to the blood vessel size, it is possible to provide a more realistic simulation since the number of diversions of a blood vessel is increased to the periphery of the blood vessel.

In addition to the above-described embodiments of this invention, the method of this invention is applicable to images obtained by diagnostic imaging apparatuses other than the X-ray CT apparatus, such as an MRI imaging apparatus and a supersonic diagnostic apparatus. Also, the object organ is not limited to the liver which is used in the above-described embodiments, and the invention is applicable to many parts of a human body.

Though the plural embodiments have been described in accordance with this invention, this invention is not limited by the embodiment, and all of technical contents for realizing the technical ideas recited in claims are encompassed by this invention.

INDUSTRIAL APPLICABILITY

The medical image display method and apparatus of this invention assist doctors in conducting diagnoses and therapies by displaying a flow of a contrast agent in a blood vessel in a pseudo manner.

The invention claimed is:

1. A medical image display method comprising:
   an organ display step for displaying an image of a predetermined organ including a desired blood vessel in a medical image on a display unit;
   a blood vessel selection step for selecting the desired blood vessel from the image of the predetermined organ displayed by the organ display step and designating a specific position of the desired blood vessel; and
   an image display step for displaying a simulation image on which is observable a pseudo flow of a virtual contrast agent through the blood vessel selected in the blood vessel selection step, on the image of the predetermined organ.

2. The medical image display method according to claim 1, further comprising:
   a tissue border calculation step for calculating a tissue border of a related region relating to the desired blood vessel selected by the blood vessel selection step, wherein
   the image display step in the pseudo imaging mode enables to display a pseudo image as if the contrast agent were made to flow from the specified position to the selected blood vessel and the related region of the blood vessel based on the tissue border calculated by the tissue border calculation step.

3. The medical image display method according to claim 1, wherein the image display step in the pseudo imaging mode-comprises sequentially displaying the pseudo flow of the contrast agent from the specified-position to the related region calculated by the tissue border calculation step.

4. The medical image display method according to claim 1, wherein the blood vessel selection step comprises setting a region of interest in extracting the image of the predetermined organ and the tissue border calculation step comprises calculating the tissue border based on the set region of interest.

5. The medical image display method according to claim 1, wherein the blood vessel selection step comprises arbitrarily setting the specified position in the desired blood vessel as a virtual contrast agent injection start position.

6. The medical image display method according to claim 5, further comprising a step for setting a termination position corresponding to the flow start position, wherein the image display step in the pseudo imaging mode comprises sequentially displaying a pseudo image of a flow of the contrast agent from the injection start position to the termination position.

7. The medical image display method according to claim 1, wherein the image display step in the pseudo imaging mode comprises sequentially displaying a pseudo image of a flow of the contrast agent to a substantially whole part of the related region of the selected blood vessel.

8. The medical image display method according to claim 1, wherein the image display step in the pseudo imaging mode comprises sequentially highlighting a locus of the flow of the contrast agent in displaying the pseudo image.

9. The medical image display method according to claim 8, wherein the highlighting comprises marking out the locus with a predetermined color or luminance.

10. The medical image display method according to claim 1, wherein the image display step in the pseudo imaging mode comprises sequentially displaying a pseudo image of a flow of the contrast agent from the predetermined position of the blood vessel selected by the blood vessel selection step to a periphery of the blood vessel.

11. A medical image display apparatus comprising:
an organ display unit for displaying an image of a predetermined organ including a desired blood vessel in a medical image on a display unit;
a blood vessel selection unit for selecting the desired blood vessel from the image of the predetermined organ displayed by the organ display unit and designating a specific position of the desired blood vessel; and
an image display unit for displaying a simulation image on which is observable a pseudo flow of a virtual contrast agent through the blood vessel selected in the blood vessel selection unit, on the image of the predetermined organ.

12. The medical image display apparatus according to claim 11, further comprising:
a tissue border calculation unit for calculating a tissue border of a related region relating to the desired blood vessel selected by the blood vessel selection unit, wherein
the image display unit in the pseudo imaging mode enables to display a pseudo image as if the contrast agent were made to flow from the specified position through the selected blood vessel and to the related region of the blood vessel based on the tissue border calculated by the tissue border calculation unit.

13. The medical image display apparatus according to claim 11, wherein the image display unit in the pseudo imaging mode comprises sequentially displaying a pseudo flow of the contrast agent from the specified position to the related region calculated by the tissue border calculation unit.

14. The medical image display apparatus according to claim 11, wherein
the blood vessel selection unit comprises setting a region of interest in extracting the image of the predetermined organ and
the tissue border calculation unit comprises calculating the tissue border based on the set region of interest.

15. The medical image display apparatus according to claim 11, wherein the blood vessel selection unit comprises arbitrarily setting the specified position in the blood vessel as a virtual contrast agent injection start position.

16. The medical image display apparatus according to claim 15, further comprising a unit for setting a termination position corresponding to the injection start position, wherein
the image display unit in the pseudo imaging mode comprises sequentially displaying a pseudo image of a flow of the contrast agent from the injection start position to the termination position.

17. The medical image display apparatus according to claim 11, wherein the image display unit in the pseudo imaging mode comprises sequentially displaying a pseudo image of a flow of the contrast agent to a substantially whole part of the related region of the selected blood vessel.

18. The medical image display apparatus according to claim 11, wherein the image display unit in the pseudo imaging mode comprises sequentially highlighting a locus of the flow of the contrast agent in displaying the pseudo image.

19. The medical image display apparatus according to claim 18, wherein the highlighting comprises marking out the locus with a predetermined color or luminance.

20. The medical image display apparatus according to claim 11, wherein the image display unit in the pseudo imaging mode comprises sequentially displaying a pseudo image of a flow of the contrast agent from the predetermined position of the blood vessel selected by the blood vessel selection unit to a periphery of the blood vessel.

* * * * *